(12) United States Patent
Warrington et al.

(10) Patent No.: US 6,809,120 B1
(45) Date of Patent: Oct. 26, 2004

(54) COMPOSITION CONTAINING PROPARGYLAMINE FOR ENHANCING CANCER THERAPY

(75) Inventors: R. C. Warrington, Saskatoon (CA); I. Alick Paterson, deceased, late of Saskatoon (CA), by Brenda Kennedy, Kevin Rogers, legal representatives; Alan A. Boulton, Saskatoon (CA)

(73) Assignee: University of Saskatchewan Technologies Inc., Saakatoon (CA)

( * ) Notice: Subject to any disclaimer, the term of this patent is extended or adjusted under 35 U.S.C. 154(b) by 0 days.

(21) Appl. No.: 09/600,125

(22) PCT Filed: Jan. 13, 1999

(86) PCT No.: PCT/CA99/00005

§ 371 (c)(1),
(2), (4) Date: Apr. 10, 2002

(87) PCT Pub. No.: WO99/36076

PCT Pub. Date: Jul. 22, 1999

Related U.S. Application Data (60) Provisional application No. 60/071,023, filed on Jan. 13, 1998.

(51) Int. Cl.$^7$ ............................................. A61K 31/13
(52) U.S. Cl. ......................... 514/671; 514/23; 514/25; 514/27; 514/34; 514/49; 514/110; 514/269; 514/274; 514/672; 514/922
(58) Field of Search ................... 514/671, 672, 514/23, 25, 27, 38, 49, 110, 269, 274

(56) References Cited

U.S. PATENT DOCUMENTS

| | | | |
|---|---|---|---|
| 4,460,599 A | | 7/1984 | Remers |
| 5,169,868 A | | 12/1992 | Davis et al. |
| 5,840,979 A | * | 11/1998 | Durden et al. ............... 564/409 |
| 6,239,181 B1 | * | 5/2001 | Bobotas ....................... 514/654 |
| 6,465,448 B1 | * | 10/2002 | Gerson et al. ............... 514/183 |

OTHER PUBLICATIONS

Warrington, R.C. et al., "Modulation of anticancer drug toxicity by L–histidinol: A route for improving human cancer chemotherapy?", Drugs of the Future, 1993, pp. 743–749.

Warrington, R.C. et al., "L–Histidinol in experimental chemotherapy: improving the selectivity and efficacy of anti-cancer drugs, eliminating metastatic disease and revering the multi–drug resistant phenotype", Biochemistry & Cell Biology, 1992, pp. 365–375, vol. 70.

Warrington, R.C. et al., "Hitidinol–Mediated Enhancement of the Specificity of Two Anticancer Drugs in Mice Bearing Leukemic Bone Marrow Disease", Journal of the National Cancer Institute, 1985, pp. 1070–1077, vol. 71.

K. Tipton, C. Mothersill, R. Mooney. "Cytoprotective Agents comprising monoamine oxidase inhibitors". PCT International Publication No. 98/40102; International Publication date Sep. 17, 1998; Priority Date: Mar. 13, 1997.

K. Tipton, C. Mothersill, R. Mooney. "Cell protection by 1–deprenyl". Abstract for: 9th Amine Oxidase Workshop, Jul. 2000, Barcelona, Spain.

S. ThyagaRajan, S.Y. Felten, D.L. Felten. "Antitumor effect of L–deprenyl in rats with carcinogen–induced mammary tumors." (1998).

* cited by examiner

*Primary Examiner*—Frederick Krass
(74) *Attorney, Agent, or Firm*—Bereskin & Parr (57) ABSTRACT

Antineoplastic drug modulators are described. The specific modulators referred to are propargylamines which can enhance the cytotoxic effects of antineoplastic drugs on cancer cells while protecting normal cells from damage. The propargylamine modulators can be used to increase the selectivity and effectiveness of conventional antineoplastic drugs, to reduce the unwanted side-effects of cancer chemotherapy, to improve effectiveness of cancer chemotherapy, to improve treatment of cancers for which treatment is otherwise ineffective, to improve therapy of cancers otherwise unresponsive or poorly responsive due to drug-resistance and/or toxicity limited treatment regimens and to render effective chemotherapy for previously untreatable cancers.

53 Claims, 3 Drawing Sheets

COMPOSITION CONTAINING PROPARGYLAMINE FOR ENHANCING CANCER THERAPY

RELATED APPLICATIONS

The present application is the national phase entry of PCT patent application Ser. No. PCT/CA99/00005, filed on Jan. 13, 1999 and claims the benefit of priority under 35 U.S.C. §119(e) from U.S. provisional patent application No. 60/071,023, filed on Jan. 13, 1998.

FIELD OF THE INVENTION

The present invention relates to a method for enhancing cancer therapy by administering an effective amount of an antineoplastic modulator. Preferred antineoplastic modulators are propargylamines including aliphatic propargylamines and aromatic propargylamines. The invention also includes a pharmaceutical composition for enhancing the treatment of cancer comprising an effective amount of an antineoplastic modulator of the present invention in admixture with a suitable diluent or carrier.

BACKGROUND OF THE INVENTION

Cancer is a collection of diseases involving inappropriate and unregulated growth of cells in the body. The aim of chemical therapy (chemotherapy) of cancer is to introduce a chemical (antineoplastic drug) which will kill the cancerous cells but will not damage normal cells. The early rationale for the development of conventional antineoplastic drugs was that such agents would act selectively on cells undergoing cell division; since cancerous cells were thought to be invariably dividing more rapidly than normal cells in the body, it was believed that this would offer some therapeutic selectivity. However, antineoplastic agents collectively have the lowest therapeutic indices of any class of drugs used in humans. This lack of selectivity leads to the severe side effects associated with cancer chemotherapy; the major dose-limiting consideration for use of these agents is toxicity to bone marrow. Furthermore, the poor selectivity of these agents means they must be used at sub-optimal doses. The latter, in turn, may cause the development of a variety of drug resistance traits by cancerous cells. Thus, many types of cancers are ultimately unresponsive to chemotherapy and are therefore incurable.

Notwithstanding such limitations, chemotherapy remains the only and thus the most important treatment option for disseminated cancers. Despite decades of effort to find more effective and less toxic agents, the poor response of patients to conventional anticancer drugs and the limitations arising from intrinsic or acquired drug-resistance continue to limit the chemotherapeutic approach. It is estimated that over 50% of patients with advanced cancer will fail to respond, or will relapse from their initial response to chemotherapy, and will thus ultimately succumb to their disease. Given the prevalence and severity of disseminated disease, improving the chemotherapeutic treatment modality nevertheless remains a crucial objective of cancer research (1).

One novel and potentially major means of improving the chemotherapeutic modality of cancer treatment would be to improve the selectivity of the currently-available agents. To the degree to which selectivity could be improved, such an approach would diminish the toxic side effects and allow treatment with more appropriate doses of antineoplastics which, in turn, would diminish the inadvertent selection of drug-resistance variants during treatment. If, in addition, such a strategy would circumvent drug-resistance traits of either the intrinsic or acquired types, it would diminish all of the major, known limitations to conventional cancer chemotherapy. Remarkably, such an approach has been developed and verified to have all of these advantages in experimental chemotherapeutic models (2–17). Termed the modulator approach for improving cancer chemotherapy, this novel strategy solves the major limitations otherwise associated with the use of conventional antineoplastics.

An antineoplastic modulator is a chemical which modifies the action of an antineoplastic drug, improving the selectivity, and therefore efficacy of the antineoplastic drug. An antineoplastic modulator acts, simultaneously, to advantage in three ways: i), it protects non-cancerous (normal) tissue from the toxic effects of the antineoplastic drug; ii), it increases the ability of the antineoplastic drug to kill cancerous cells, and iii), it suppresses the drug resistance traits exhibited by many cancerous cells.

The present inventors have prepared many novel propargylamines as described in U.S. Pat. Nos. 5,169,868 and 5,840,979. The inventors have shown that the novel propargylamines are useful as MAO-B inhibitors and are useful in treating various neuropsychiatric disorders including Parkinson's disease, Alzheimer's disease, depression, attention deficit disorder, hyperactive disorders as well as other aging-associated diseases.

Surprisingly, the present inventors have found that the propargylamines are also useful as antineoplastic modulators and can enhance the effect of antineoplastic drugs.

SUMMARY OF THE INVENTION

Broadly stated, the present invention relates to a method of enhancing cancer therapy by administering an effective amount of a propargylamine. The present inventors have shown that propargylamines enhance the killing of tumor cells by antineoplastic drugs and protect normal cells from the cytotoxic effects of antineoplastic drugs. Consequently, propargylamines are well-suited to enhance any chemotherapy regime and can increase the effectiveness while reducing the side-effects of cancer therapy.

In one aspect, the present invention relates to a method for enhancing the effect of an antineoplastic drug comprising administering an effective amount of a propargylamine to an animal in need thereof.

In another aspect, the present invention relates to a method of increasing the sensitivity of a tumor to an antineoplastic drug comprising administering an effective amount of propargylamine of the invention to an animal in need thereof.

In a further aspect, the present invention provides a method of protecting normal cells from the cytotoxic effects of an antineoplastic drug comprising administering an effective amount of a propargylamine of the invention to an animal in need thereof.

In a further aspect, the present invention relates to a method for treating cancer comprising administering an antineoplastic drug and an effective amount of a propargylamine of the invention to an animal in need thereof.

The present invention also includes a use of a propargylamine of the present invention for the preparation of a medicament to be used in the therapeutic methods described herein.

The present invention further includes a pharmaceutical composition useful for enhancing cancer therapy comprising an effective amount of a propargylamine of the invention in admixture with a suitable diluent or carrier.

The pharmaceutical compositions of the present invention may be useful in (i) enhancing the activity of an antineoplastic drug, (ii) increasing the sensitivity of a tumor to an antineoplastic drug and/or (iii) protecting normal cells from the cytotoxic effects of an antineoplastic drug.

The present invention also includes a pharmaceutical composition useful for treating cancer comprising an antineoplastic drug and an effective amount of a propargylamine of the present invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Broadly stated, the present invention relates to a method of enhancing cancer therapy by administering an effective amount of a propargylamine. The present inventors have shown that propargylamines enhance the killing of tumor cells by antineoplastic drugs and protect normal cells from the cytotoxic effects of antineoplastic drugs. In addition, the propargylamines have been shown to overcome a drug-resistance attribute of tumor cells. In vivo data is included which verifies that these three powerful attributes of the approach are operative in live, tumor bearing animals. Consequently, propargylamines are well-suited to enhance any chemotherapy regime.

Propargylamines

The propargylamines that may be included in the methods, uses and compositions of the present invention include any propargylamine that can enhance the effect of an antineoplastic drug. The ability of a propargylamine to enhance the effect of an antineoplastic can be determined using the assays described in the Examples or using other assays known in the art.

In one embodiment, the propargylamine is of the general formula I wherein
  x is an integer ranging from 0 to 13;
  y is an integer ranging from 0 to 5;
  z is an integer ranging from 0 to 5;
  $R_1$, $R_2$ and $R_3$ are the same or different and represent hydrogen or a straight chain or branched lower alkyl; and
  R' and R" are the same or different and represent hydrogen, phenyl or a halogen and pharmaceutically acceptable salts thereof.

Preferably the lower alkyl has between 1 and 4 carbon atoms and the halogen atom is selected from fluorine, chlorine, bromine and iodine. More preferably, the lower alkyl is selected from methyl.

In another embodiment, the propargylamine is of the general formula I wherein y is 1 and the pharmaceutically acceptable salts thereof. A preferred propargylamine of the formula I wherein y is 1 is R-2-heptyl-methylpropargylamine (R-2HMP).

Other propargylamines of the formula I wherein y is 1 include:
N-(1-Propyl) N-methylpropargylamine;
N-(2-Propyl) N-methylpropargylamine;
N-(1-Butyl) N-methylpropargylamine;
N-(1-Pentyl) N-methylpropargylamine;
N-(1-Hexyl) N-methylpropargylamine;
N-(1-Heptyl) N-methylpropargylamine;
N-(1-Octyl) N-methylpropargylamine;
N-(1-Nonyl) N-methylpropargylamine;
N-(1-Decyl) N-methylpropargylamine;
N-(1-Undecyl) N-methylpropargylamine;
N-(1-Dodecyl) N-methylpropargylamine;
(R)-N-(2-Butyl) N-methylpropargylamine;
(R)-N-(2-Pentyl) N-methylpropargylamine;
(R)-N-(2-Hexyl) N-methylpropargylamine;
(R)-N-(2-Heptyl) N-methylpropargylamine;
(R)-N-(2-Octyl) N-methylpropargylamine;
(R)-N-(2-Octyl) N-methylpropargylamine;
(R)-N-(2-Decyl) N-methylpropargylamine;
(R)-N-(2-Undecyl) N-methylpropargylamine; and
(R)-N-(2-Dodecyl) N-methylpropargylamine.

In yet another embodiment, the propargylamine is of the general formula I, described above, wherein y is 0, and the pharmaceutically acceptable salts thereof. A preferred propargylamine of the formula I where y=0, is R-2-heptyl-propargylamine (R-2HPA).

Other compounds of the formula I, wherein y is 0, include:
N-(1-Propyl) propargylamine;
N-(2-Propyl) propargylamine;
N-(1-Butyl) propargylamine;
N-(1-Pentyl) propargylamine;
N-(1-Hexyl) propargylamine;
N-(1-Heptyl) propargylamine;
N-(1-Octyl) propargylamine;
N-(1-Nonyl) propargylamine;
N-(1-Decyl) propargylamine;
N-(1-Undecyl) propargylamine;

N-(1-Dodecyl) propargylamine;
(R)-N-(2-Butyl) propargylamine;
(R)-N-(2-Pentyl) propargylamine;
(R)-N-(2-Hexyl) propargylamine;
(R)-N-(2-Heptyl) propargylamine;
(R)-N-(2-Octyl) propargylamine;
(R)-N-(2-Octyl) propargylamine;
(R)-N-(2-Decyl) propargylamine;
(R)-N-(2-Undecyl) propargylamine; and
(R)-N-(2-Dodecyl) propargylamine.

The preferred propargylamines of the chiral compounds of the formula I are the R-enantiomers.

In a further embodiment, the propargylamine is R-deprenyl. R-deprenyl is a compound of the formula I wherein $R_1$ is methyl, $R_2$ is hydrogen, R" is phenyl, R' is hydrogen, x is 1, y is 1, z is 1 and $R_3$ is hydrogen.

In another embodiment, the propargylamine is R-desmethyldeprenyl. R-desmethyldeprenyl is a compound of the formula I wherein $R_1$ is methyl, $R_2$ is hydrogen, R" is phenyl, R' is hydrogen, x is 1, y is 0, z is 1 and $R_3$ is hydrogen.

In yet another embodiment, the propargylamine is Rasagiline having the following formula II:

All of the above described propargylamines may be collectively referred to as "the propargylamines of the invention".

The propargylamines of the present invention may be prepared using techniques known in the art. For example, the aliphatic propargylamines may be prepared as described in the inventors U.S. Pat. Nos. 5,169,868 and 5,840,979 both which are incorporated herein by reference in their entirety. Briefly, the compounds may be prepared by condensing propargyl bromide with a chiral aliphatic amine or N-methylamine in the presence of a base and recovering the desired compound. Preferably the R-enantiomers are prepared.

Therapeutic Methods and Uses

As hereinbefore mentioned, the present invention relates to a method for enhancing the effect of an antineoplastic drug comprising administering an effective amount of a propargylamine of the invention to an animal in need thereof. The invention also includes a use of a propargylamine of the invention to enhance the effect of an antineoplastic drug.

The term "effective amount" as used herein means an amount effective, at dosages and for periods of time necessary to achieve the desired result.

The term "animal" as used herein means any member of the animal kingdom including all mammals, birds, fish, reptiles and amphibians. Preferably, the animal to be treated is a mammal, more preferably a human.

One method by which the propargylamines of the invention may enhance the effect of an antineoplastic drug is by increasing the sensitivity of the tumor to the drug. Accordingly, in one aspect, the present invention relates to a method of increasing the sensitivity of a tumor to an antineoplastic drug comprising administering an effective amount of propargylamine of the invention to an animal in need thereof. The tumor may be one that is resistant to cancer therapy such as a multidrug resistant tumor or a radioresistant tumor. This aspect also includes a use of a propargylamine of the invention to increase the sensitivity of a tumor to an antineoplastic agent.

Another method by which the propargylamines of the invention may enhance the effect of an antineoplastic drug is by protecting normal cells from the cytotoxic effects of the drug. Accordingly, in another aspect, the present invention provides a method of protecting normal cells from the cytotoxic effects of an antineoplastic drug comprising administering an effective amount of a propargylamine of the invention to an animal in need thereof. This aspect also includes a use of a propargylamine of the invention to protect normal cells from the cytotoxic effects of an antineoplastic drug.

In a further aspect, the present invention relates to a method for treating cancer comprising administering an antineoplastic drug and an effective amount of a propargylamine of the invention to an animal in need thereof. This aspect includes a use of (a) a propargylamine and (b) an antineoplastic drug to treat cancer.

The propargylamines of the invention can be used to enhance the treatment of all forms of cancer or malignant diseases for which chemotherapy is a bona fide treatment option. These malignancies include, but are not limited to, leukemias, lymphomas (Hodgkins and non-Hodgkins), plasmacytomas, histiocytomas, melanomas, adenomas, sarcomas, carcinomas of solid tissues, hypoxic tumours, squamous cell carcinomas, genitourinary cancers such as cervical and bladder cancer, hematopoietic cancers, head and neck cancers, and nervous system cancers. Treatment with the propargylamine modulators may allow for treatment of tumors that are resistant to chemotherapy. The latter are diverse, but one common, well-studied example is the so-called multi-drug resistant (MDR) tumor cells. MDR tumors include adenocarcinomas, neuroblastoma cells, leukemias, lymphomas, breast cancer and ovarian cancer cells. Treatment with the propargylamine modulators may also allow for more effective radiotherapy of tumours that currently respond poorly to radiotherapy such as adenocarcinomas of the bowel and lung.

Antineoplastic drugs which may be potentiated or enhanced by the propargylamine modulators can be any antineoplastic drug including known, conventional drugs as well as those yet to be identified. Examples of classes of antineoplastic agents include antimetabolites, alkylating agents, antimicrobial antineoplastics, antimicrotubule agents, cisplatinum and its derivatives and the topoisomerase interactive agents. In particular, chemotherapeutic agents amenable to this modulatory effect may include but are not limited to, adriamycin, BCNU and CCNU (i.e., bis (2-chloroethyl)-3-cyclohexyl-1-nitrosurea and 1-(2-chloroethyl)-3-cyclohexyl-1-nitrosourea, respectively, bleomycin sulfate, camptothecin, carmustine, chlorambucil, cisplatinum, cyclophospamide, cytosine arabinoside, daunomycin/daunorubicin, dacarbazine, doxorubicin, 5-fluorouracil, melphalan, mitomycin, mitoxantrone hydrochloride, etoposide, streptozocin and taxol and taxol derivatives.

Although the propargylamines of the invention may be administered before, after and/or concurrently with the antineoplastic drug, they are likely best administered prior to chemotherapy.

Pharmaceutical Compositions

The propargylamines of the invention may be incorporated into a pharmaceutical composition which may be useful in enhancing the activity of an antineoplastic drug, increasing the sensitivity of a tumor to an antineoplastic drug and/or protecting normal cells from the cytotoxic effects of an antineoplastic drug. The pharmaceutical composition may additionally include an antineoplastic drug and may be useful for treating cancer.

The pharmaceutical compositions of the invention can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). The pharmaceutical compositions of the invention can be for oral, topical, rectal, parenteral, local, intravenous, inhalant or intracerebral use. They may be in solid or semisolid form, for example pills, tablets, creams, gelatin capsules, capsules, suppositories, soft gelatin capsules, gels, membranes, tubelets. For parenteral and intracerebral uses, those forms for intramuscular or subcutaneous administration can be used, or forms for infusion or intravenous or intracerebral injection can be used, and can therefore be prepared as solutions of the active compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered. Dosages to be administered depend on individual needs, on the desired effect and on the chosen route of administration, but daily dosages to humans by subcutaneous, intramuscular, intravenous or intracerebral injection generally vary between about 100 ng and 100 $\mu$g of active substance per Kg body weight, preferably between 1 $\mu$g and 50 $\mu$g per Kg body weight for the aliphatic propargylamines. For aromatic propargylamines, the above doses may be increased ten fold.

The following non-limiting examples are illustrative of the present invention:

EXAMPLES

Example 1

In Vitro Protocol for Assessing the Capacity of Various Compounds to Modulate Cisplatinum Toxicity The protocol detailed below can be used for any normal/tumorigenic cell pair which will attach to plastic. Non-adherent lines (which includes most tumor cells, including NW16; consult references 5–10) require quantitation in soft agar. The present experiments are based on i) rat2 cells, a phenotypically normal, established rat fibroblast line and, ii) a tumorigenic derivative thereof, NW16 cells, which are rat2 cells transformed by a Fujinami sarcoma virus oncogene (see work of A. Pawson and P130$^{gag\text{-}fps}$). Rat2 and NW16 cells are maintained in a sub-confluent randomly-proliferating state in Dulbecco's modified minimal essential media with 10% (vol/vol) calf serum in plates incubated at 37° C. in a humidified $CO_2$ (10%) incubator. All experiments reported rely on clonogenic cell survival assays (see references 4–6). Assays using rat2 (normal cells) were performed as follows: cells are exposed, in 10 cm culture dishes, to various drugs in media plus serum for varying lengths of time; seeding is at varying cell numbers, over $log_{10}$ ranges, depending upon the degree of killing anticipated. [For the figure presented, incubation was for 72 hours prior to washing and assessment of clonogenic survival]. Both control and the experimental cultures are then gently washed, twice, with phosphate buffered saline, then once more with media minus serum, and then left in media plus serum, undisturbed until macroscopic colonies appear (7–9 days of incubation). The colonies are then fixed and stained with saturated methylene blue in 50% methanol and counted. The number of colonies, evaluated from 2 or more sets of duplicate cultures seeded at initial densities differing by factors of 10, are determined and converted to relative number of colonies, using the 0-hour control value as 1.0. Assays of NW16 cells were similar; however, because these cells are poorly adherent, following drug exposure, the washing procedure is modified, as is the quantitation of survivors step. In the latter case, quantitation requires plating the cells in soft agar (references 5–10).

Presentation of Results by "RATIO" Method

Figure 1:
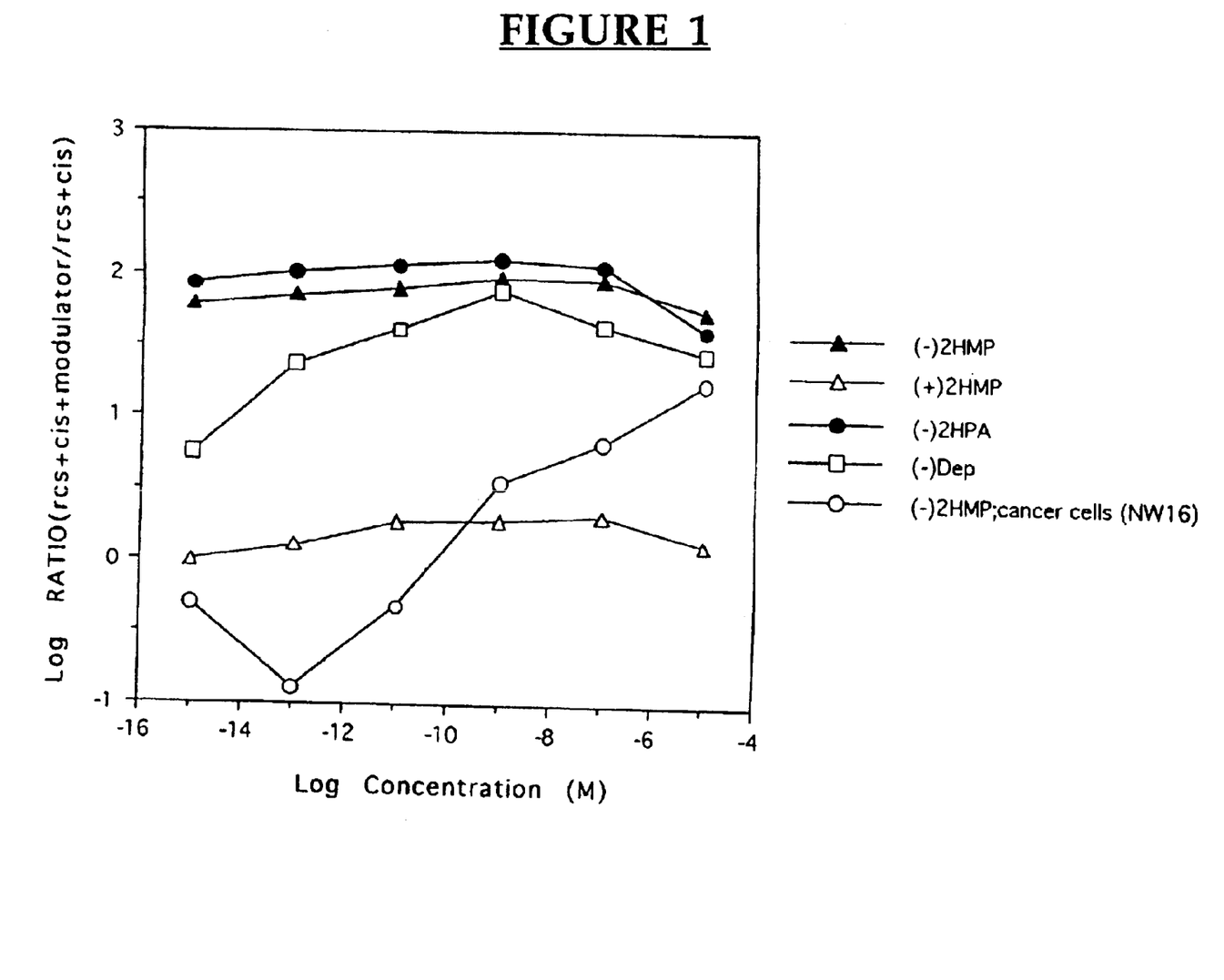
FIG. 1 is graph showing the RATIO of various antineoplastic modulators versus the concentration of the antineoplastic modulator. The definition of RATIO is provided in Example 1.

A simplified presentation of the data, by the RATIO method, is show in FIG. 1. By dividing the relative cell survival (R.C.S.) value obtained in cultures which have been exposed to the combination of anticancer drug (in this case, cisplatinum) and modulator by the corresponding R.C.S. value obtained for the anticancer drug alone reveals both the nature and the magnitude of the effect mediated by the modulator. Ratios greater than unity indicate that the modulator has conferred a protective response, whereas ratios less than unity indicate an enhanced cell killing.

Results

As can be seen from FIG. 1, R-2-heptyl-propargylamine (R-2HPA), the desmethyl metabolite of R-2-heptyl-methyl propargylamine (R-2HMP), and R-2HMP (the pro-drug) are effective, over a wide concentration range ($10^{-7}$–$10^{-15}$ M), at protecting normal fibroblasts which are p53 dependent. R-2BPA is the more potent. R-Deprenyl whilst active, is less efficacious over a more limited concentration range ($10^{-7}$–$10^{-13}$ M). The usually inactive pro-drug isomer S-2HMP is also inactive in this assay. In the tumorigenic cells (mutants in which p53 is absent) it can be seen that enhanced killing by cisplatinum occurs in the range ($10^{-11}$–$10^{-15}$ M) but with a reversal to a protective effect when the concentration of R-2HMP is $10^{-9}$M or greater.

Summary

R-2HMP and R-2HPA both protect normal cells and enhance the killing of tumor cells in the presence of cisplatinum in this in vitro fibroblast model. The protection and the enhanced killing occur in the $10^{-11}$–$10^{-15}$ M range. R-Deprenyl was also effective over a more limited concentration, in the $10^{-7}$ to $10^{-13}$ M range. Since L-histidinol exhibits similar properties (although higher doses are required) in this and several other in vitro and in vivo paradigms, and in the presence of other anticancer drugs, it is reasonable to predict that R-2HMP, R-2HPA and the other aliphatic propargylamines, by analogy, will also exhibit activity in these other systems.

Example 2

In Vivo Assessment of Anticancer Drug Modulators: Effects of R-2HPA

Seven groups of mice were treated and assessed in this model as follows:

1. Nil control (1 mouse)
2. P388 control (1 mouse)
3. Cisplatinum (5 mice)
4. Histidinol (2 mice)
5. Histidinol+cisplatinum (5 mice)
6. R-2HPA (4 mice)
7. R-2HPA+cisplatinum (5 mice)

P388 cells (1 million) were injected into the tail vein of 22 female DBA/2J mice (Protocol first developed in reference 6 and 8). The mice were then randomly divided into the above groups and injected (ip) with drugs 96 h later. Doses were cisplatinum 0.2 mg at 0 hour; Histidinol 5 mg/injection and R-2HPA 0.38 ug/injection; administered 5 times at -2, 0, +2, +4, and +6 hours. 48 h after drug treatment, cells from the femurs of the mice were harvested, washed and plated (at log10 dilutions) so as to allow quantitative and specific relative cell survival values to be generated for the responses of normal femoral bone marrow cells (specifically, CFU-C/GM or granulocyte/macrophage precursor cells) and clonogenic P388 leukemia cells (8).

Figure 2:
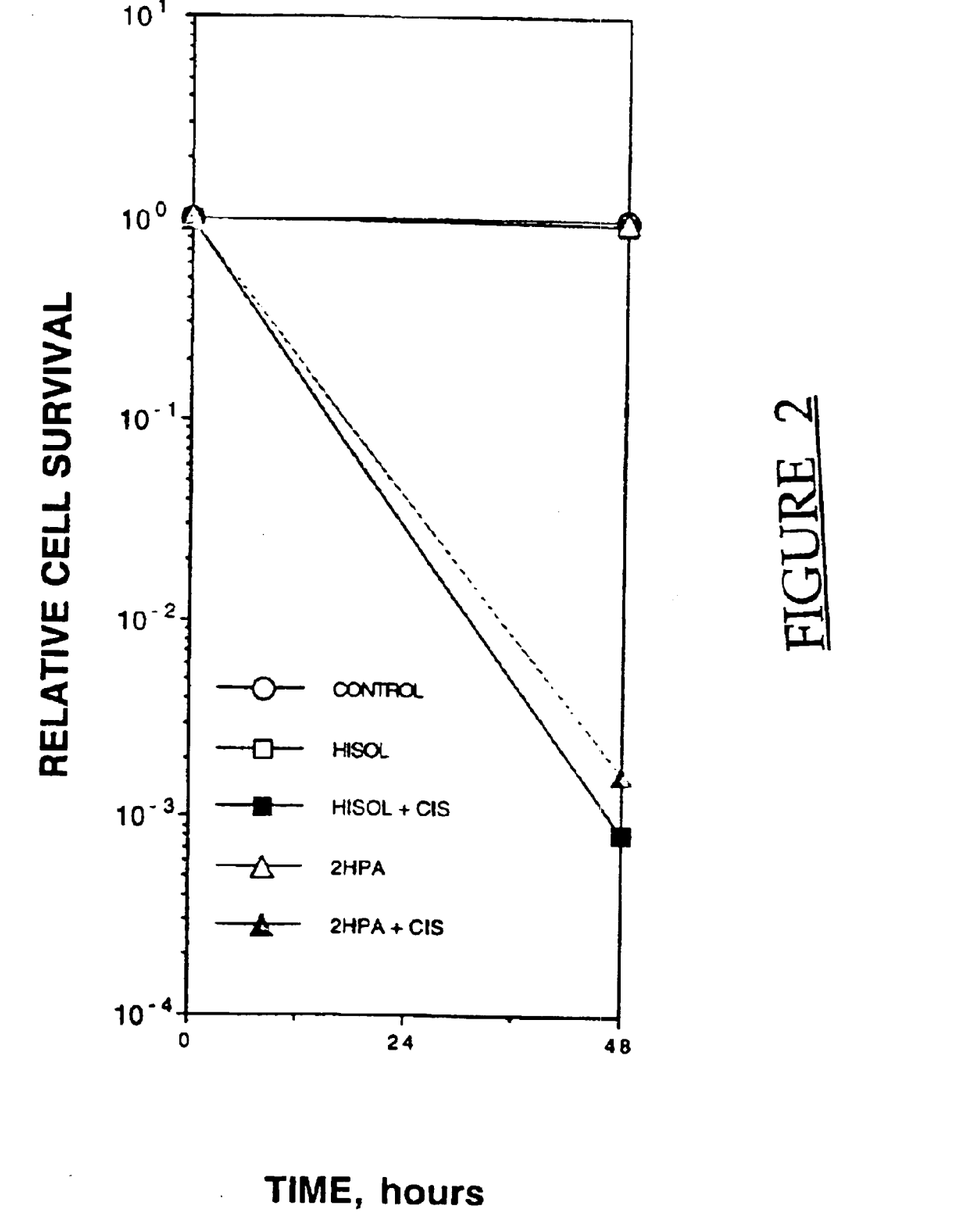
FIG. 2 is a graph showing the relative cell survival of normal bone marrow versus time, in the presence of various modulators. HISOL=histindinol, cis=cisplatinum, 2HPA=R-2HPA.
Figure 3:
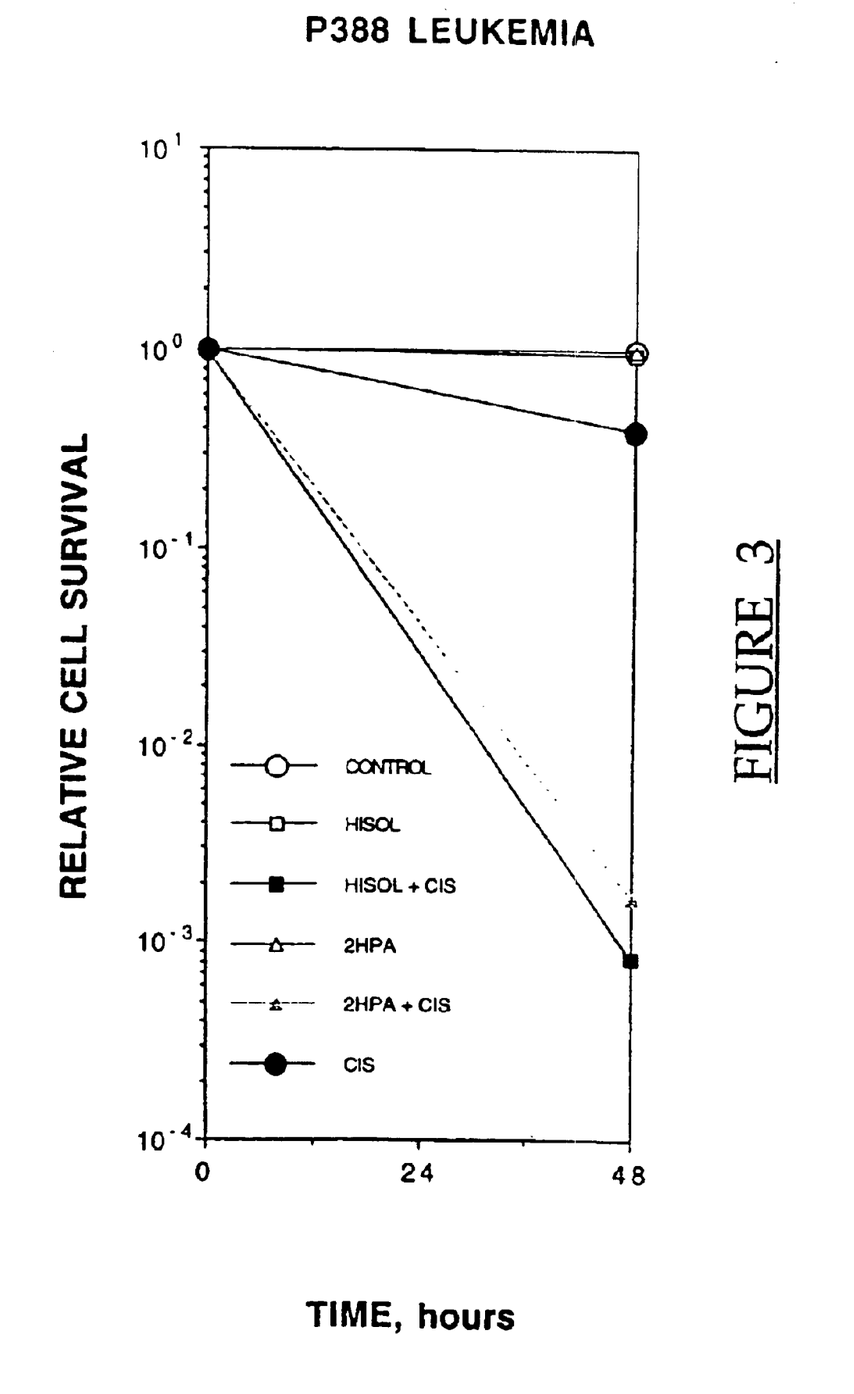
FIG. 3 is a graph showing the relative cell survival of cancer cells versus time, in the presence of various modulators.

As can be seen in FIG. 2, both histidinol and R-2HPA were effective at protecting normal bone marrow cells, whereas in FIG. 3, it can be seen that both histidinol and R-2HPA enhanced the killing by cisplatinum of P388 cells. It should be emphasized that the P388 leukemic line is substantially resistant to the cisplatinum (relative to the responses of the CFU-c/GM cells). This is an example of the poor therapeutic index common to conventional antineoplastics. In this example, the cisplatinum, when used alone, can be seen to be about 100-times more effective at killing the crucial normal marrow cells than it is for killing the intrafemoral leukemia (tumor) cells. In the presence of the modulators histidinol and R-2HPA, the therapeutic index of cisplatinum is vastly improved; thus, the toxicity to the marrow cells is essentially eliminated and the toxicity to the leukemia cells is increased by almost a 1000-fold. In other words, both histidinol and R-2HPA are simultaneously protecting the most vulnerable normal cells from cancer drug toxicity and simultaneously circumventing a profound drug-resistance trait. That these effects are observed in vivo (i.e., in live animals) and in the same tissue of those animals cannot be over-emphasized in terms of its potential capacity to improve chemotherapy, in as much as it reveals clearly and dramatically the ability of modulators to improve selectivity, efficacy and to circumvent the problem of drug-resistance shown by tumor cells. It can also be seen that this remarkable effect is obtained with R-2HPA at the low dose of 0.38 ug, producing a therapeutic index of about 50,000 between the protection of healthy normal cells and the killing of the cancerous cells. This effect is known to be p53 dependent vis a vis histidinol and it is likely to be the same with R-2HPA.

The modulator strategy has been shown to be remarkably effective in many in vivo tumor models (4–6; 7–11), in numerous types of human cancer cells (12,13) and in many kinds of drug resistance traits (5; 16,17). Consequently, considering the data cited herein, it is predicted that the use of propargylamines as antineoplastic modulators will improve the chemotherapeutic management of a wide variety of human malignant disease types which will include non-resistant, intrinsic and acquired drug-resistance types. The modulator approach has been validated experimentally to markedly improve treatment of malignancies of myeloid origin (leukemias, lymphomas, and cancers of "blood cell" origin; (7–10) and for disseminated or metastatic disease (11); these are the situations wherein chemotherapy is often the only available clinical treatment option, the least responsive to treatment and/or the most prone to failure due to either intrinic or acquired drug-resistance and hence incurable status.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and fan individually indicated to be incorporated by reference in its entirety.

FULL CITATIONS FOR REFERENCES REFERRED TO IN THE SPECIFICATION

1) M R Grever and B A Chabner, Cancer Drug Discovery and Development. in: *Cancer: Principles and Practice of Oncology*, 5th Ed., V T DeVita, S Hellman and S A Rosenberg, editors. Lippincott-Raven Press 1997.
2) R C Warrington, 1978. Selective Killing of Oncogenic Human Cells Cocultivated with Normal Human Fibroblasts. *Journal of the National Cancer Institute*, 61, 69–72.
3) R C Warrington and W. D. Fang 1982. Protection of Cultured Mouse Spleen Cells From the Cytotoxic Action of AraC and 5FU by L-Histidinol. *Journal of the National Cancer Institute*, 68, 279–286.
4) R C Warrington, 1993. Modulation of anticancer drug toxicity by L-histidinol; a route for improving human cancer chemotherapy? *Drugs of the Future*, 18, 743–749.
5) R C Warrington, 1992. L-Histidinol in Experimental Cancer Chemotherapy: Improving the Selectivity and Efficacy of Anticancer Drugs, Eliminating Metastatic Disease and Reversing the Multidrug-Resistant Phenotype. *Biochemistry and Cell Biology* 70, 365–375.
6) R C Warrington, 1986. A Novel Approach for Improving the Efficacy of Experimental Cancer Chemotherapy using Combinations of Anticancer Drugs and L-histidinol. *Anticancer Research*, 6, no. 3, 451–464.
7) R. C. Warrington, T. G. Muzyka and W. D. Fang, 1984. Histidinol-Mediated Improvement in the Specificity of 1-β-D-arabinofuranosylcytosine and 5-fluorouracil in L1210 Leukemia Bearing Mice. *Cancer Research*, 44, 2929–2937.
8) R. C. Warrington and W. D. Fang, 1985. Histidinol-mediated Enhancement of the Specificity of Two Anticancer Drugs in Mice Bearing Leukemic Bone Marrow Disease. *Journal of the National Cancer Institute*, 74, 1071–1077.
9) R. C. Warrington, I Cheng and W. D. Fang, 1985. Effects of L-histidinol on the susceptibility of P815 mastocytoma cells to selected anticancer drugs in vitro and in vivo. *Journal of the National Cancer Institute*, 78: 11177 1183.
10) R. C. Warrington and W. D. Fang, 1989. L-Histidinol Improves the Selectivity and Efficacy of Alkylating Agents and Daunomycin in Mice with P388 Leukemia. *British Journal of Cancer*, 60, 652–656, 1989.

11) R. C. Warrington and W. D. Fang, 1991. Improved treatment of disseminated B 16f10 melanoma in mice with anticancer drugs in combination with L-histidinol. *Anticancer Research* 11, 1869–1874.

12) R C Warrington, I Cheng, L Zhang and W D Fang, 1993. L-Histidinol increases the vulnerability of cultured human leukemia and lymphoma cells to anticancer drugs. *Anticancer Res.* 13: 2107–2112.

13) R C Warrington, I Cheng and W D Fang, 1994. Susceptibility of human colon carcinoma cells to anticancer drugs is enhanced by L-histidinol. *Anticancer Research*, 14: 367–372.

14) R C Warrington, W D Fang, L Zhang, M Shieh and M H Saier, 1996. L-Histidinol selectively modulates daunomycin toxicity in normal and tumorigenic kidney epithelial cells. *Anticancer Res.* 16: 3629–3634.

15) R C Warrington, W D Fang, L Zhang, M Shieh and M H Saier, 1996. Mimetics of L-histidinol which selectively modulate daunomycin toxicity in normal and tumorigenic epithelial cells. *Anticancer Res.* 16: 3635–3640.

16) R C Warrington and W. D. Fang, 1989. Reversal of the Multidrug-Resistant Phenotype of Chinese Hamster Ovary Cells by L-histidinol. *Journal of the National Cancer Institute*, 81, 798–803

17) R C Warrington, W D Fang and L Zhang, 1996. L-Histidinol reverses resistance of cisplatinum and other antineoplastics in a tumorigenic epithelial cell line. *Anticancer Res.* 16: 3641–3645.

We claim:

1. A method for enhancing the activity of an antineoplastic drug comprising administering, before, after or concurrently with said drug, an effective amount of a propargylamine to an animal in need thereof, wherein the propargylamine is of the general formula I $$R''(CR'_2)_xC\underset{R_2}{\overset{R_1}{|}}N\diagup\diagdown\begin{array}{c}(CH_2)_yH\\(CH_2)_zC\equiv CR_3\end{array}$$

wherein x is an integer ranging from 0 to 13;
y is an integer ranging from 0 to 5;
z is 1;
$R_1$, $R_2$ and $R_3$ are the same or different, or represent hydrogen or a straight chain or branched lower alkyl; and
R' and R" are the same or different, or represent hydrogen, phenyl or a halogen and pharmaceutically acceptable salts thereof.

2. A method for increasing the sensitivity of a tumor to an antineoplastic drug comprising administering, before, after or concurrently with said drug, an effective amount of a propargylamine to an animal in need thereof, wherein the propargylamine is of the general formula I $$R''(CR'_2)_xC\underset{R_2}{\overset{R_1}{|}}N\diagup\diagdown\begin{array}{c}(CH_2)_yH\\(CH_2)_zC\equiv CR_3\end{array}$$

wherein x is an integer ranging from 0 to 13;
y is an integer ranging from 0 to 5;
z is 1;
$R_1$, $R_2$ and $R_3$ are the same or different and represent hydrogen or a straight chain or branched lower alkyl; and
R' and R" are the same or different and represent hydrogen, phenyl or a halogen, or pharmaceutically acceptable salts thereof.

3. A method according to claim 2 wherein the tumor is a drug resistant tumor.

4. A method for protecting normal cells from the cytotoxic effects of an antineoplastic drug comprising administering, before, after or concurrently with said drug, an effective amount of a propargylamine to an animal in need thereof, wherein the propargylamine is of the general formula I $$R''(CR'_2)_xC\underset{R_2}{\overset{R_1}{|}}N\diagup\diagdown\begin{array}{c}(CH_2)_yH\\(CH_2)_zC\equiv CR_3\end{array}$$

wherein x is an integer ranging from 0 to 13;
y is an integer ranging from 0 to 5;
z is 1;
$R_1$, $R_2$ and $R_3$ are the same or different and represent hydrogen or a straight chain or branched lower alkyl; and
R' and R" are the same or different and represent hydrogen, phenyl or a halogen, or pharmaceutically acceptable salts thereof with the proviso that the propargylamine is not R-deprenyl or R-desmethyldeprenyl.

5. A method according to claim 1 wherein y is 1.

6. A method according to claim 5 wherein the propargylamine is R-2 heptyl-methyl propargylamine (R-2HMP).

7. A method according to claim 1 wherein the propargylamine is selected from the group consisting of N-(1-Propyl) N-methylpropargylamine; N-(2-Propyl) N methylpropargylamine; N-(1-Butyl) N-methylpropargylamine; N-(1-Pentyl) N methylpropargylamine; N-(1-Hexyl) N-methylpropargylamine; N-(1-Heptyl) N methylpropargylamine; N-(1-Octyl) N-methylpropargylamine; N-(1-Nonyl) N methylpropargylamine; N-(1-Decyl) N-methylpropargylamine; N-(1-Undecyl) N methylpropargylamine; N-(1-Dodecyl) N-methylpropargylamine; (R)-N-(2-Butyl) N methylpropargylamine; (R)-N-(2-Pentyl) N-methylpropargylamine; (R)-N-(2-Hexyl) N methylpropargylamine; (R)-N-(2-Heptyl) N-methylpropargylamine; (R)-N-(2-Octyl) N methylpropargylamine; (R)-N-(2-Octyl) N-methylpropargylamine; (R)-N-(2-Decyl) N methylpropargylamine; (R)-N-(2-Undecyl) N-methylpropargylamine; and (R)-N-(2-Dodecyl) N-methylpropargylamine.

8. A method according to claim 1, wherein y is 0.

9. A method according to claim 8 wherein the propargylamine is R 2-heptyl-propargylamine (R-2 HPA).

10. A method according to claim 8 wherein the propargylamine is selected from the group consisting of N-(1-Propyl) propargylamine; N-(2-Propyl) propargylamine; N-(1-Butyl) propargylamine; N-(1-Pentyl) propargylamine; N-(1-Hexyl) propargylamine; N-(1-Heptyl) propargylamine; N-(1-Octyl) propargylamine; N-(1-Nonyl) propargylamine; N-(1-Decyl) propargylamine; N-(1-Undecyl) propargylamine; N-(1-Dodecyl) propargylamine; (R)-N-(2-Butyl) propargylamine; (R)-N-(2-Pentyl) propargylamine; (R)-N-(2-Hexyl) propargylamine; (R)-N-(2-Heptyl) propargylamine; (R)-N-(2-Octyl) propargylamine; (R)-N-(2-Octyl) propargylamine; (R)-N-(2-Decyl) propargylamine;

(R)-N-(2-Undecyl) propargylamine; and (R)-N-(2-Dodecyl) propargylamine.

11. A method according to claim 1 wherein the propargylamine is R-deprenyl.

12. A method according to claim 1 wherein the propargylamine is R desmethyldeprenyl.

13. A method according to claim 1 wherein the animal is a human.

14. A method for enhancing the activity of an antineoplastic drug comprising administering, before, after or concurrently with said drug, an effective amount of Rasagiline to an animal in need thereof.

15. A method according to claim 1 wherein the propargylamine is a chiral compound and is the R-enantiomer.

16. A method for treating cancer comprising administering an antineoplastic drug and, before, after or concurrently with said drug, an effective amount of a propargylamine to an animal in need thereof, wherein the propargylamine is of the general formula I wherein
x is an integer ranging from 0 to 13;
y is an integer ranging from 0 to 5;
z is 1;
$R_1$, $R_2$ and $R_3$ are the same or different and represent hydrogen or a straight chain or branched lower alkyl; and
R' and R" are the same or different and represent hydrogen, phenyl or a halogen, or pharmaceutically acceptable salts thereof, with the proviso that the propargylamine is not R-deprenyl, R-desmethyldeprenyl or Rasagaline.

17. A method according to claim 16 wherein the antineoplastic drug is selected from the group consisting of cytosine arabinoside, cis-platinum, cyclophospamide, adriamycin, daunomycin, and 5-fluorouracil.

18. A method according to claim 16 wherein the propargylamine is a chiral compound and is the R-enantiomer.

19. A pharmaceutical composition for treating cancer comprising a combination of effective amounts of an antineoplastic drug and a propargylamine of the general formula I:

wherein
x is an integer ranging from 0 to 13;
y is an integer ranging from 0 to 5;
z is 1;
$R_1$, $R_2$ and $R_3$ are the same or different and represent hydrogen or a straight chain or branched lower alkyl; and
R' and R" are the same or different and represent hydrogen, phenyl or a halogen, or pharmaceutically acceptable salts thereof, with the proviso that the propargylamine is not R-deprenyl, R-desmethyldeprenyl or Rasagiline.

20. A pharmaceutical composition according to claim 19 wherein y is 1.

21. A pharmaceutical composition according to claim 20 wherein the propargylamine is R-2-heptyl-methyl propargylamine (R-2HMP).

22. A pharmaceutical composition according to claim 20 wherein the propargylamine is selected from the group consisting of N-(1-Propyl) N methylpropargylamine; N-(2-Propyl) N-methylpropargylamine; N-(1-Butyl) N methylpropargylamine; N-(1-Pentyl) N-methylpropargylamine; N-(1-Hexyl) N methylpropargylamine; N-(1-Heptyl) N-methylpropargylamine; N-(1-Octyl) N methylpropargylamine; N-(1-Nonyl) N-methylpropargylamine; N-(1-Decyl) N methylpropargylamine; N-(1-Undecyl) N-methylpropargylamine; N-(1-Dodecyl) N methylpropargylamine; (R)-N-(2-Butyl) N-methylpropargylamine; (R)-N-(2-Pentyl) N methylpropargylamine; (R)-N-(2-Hexyl) N-methylpropargylamine; (R)-N-(2-Heptyl) N methylpropargylamine; (R)-N-(2-Octyl) N-methylpropargylamine; (R)-N-(2-Octyl) N methylpropargylamine; (R)-N-(2-Decyl) N-methylpropargylamine; (R)-N-(2-Undecyl) N methylpropargylamine; and (R)-N-(2-Dodecyl) N-methylpropargylamine.

23. A pharmaceutical composition according to claim 19, wherein y is 0.

24. A pharmaceutical composition according to claim 23 wherein the propargylamine is R-2-heptyl-propargylamine (R-2HPA).

25. A pharmaceutical composition according to claim 23 wherein said propargylamine is selected from the group consisting of N-(1-Propyl) propargylamine; N-(2-Propyl) propargylamine; N-(1-Butyl) propargylamine; N-(1-Pentyl) propargylamine; N-(1-Hexyl) propargylamine; N-(1-Heptyl) propargylamine; N-(1-Octyl) propargylamine; N-(1-Nonyl) propargylamine; N-(1-Decyl) propargylamine; N-(1-Undecyl) propargylamine; N-(1-Dodecyl) propargylamine; (R)-N-(2-Butyl) propargylamine; (R)-N-(2-Pentyl) propargylamine; (R)-N-(2-Hexyl) propargylamine; (R)-N-(2-Heptyl) propargylamine; (R)-N-(2-Octyl) propargylamine; (R)-N-(2-Octyl) propargylamine; (R)-N-(2-Decyl) propargylamine; (R)-N-(2-Undecyl) propargylamine; and (R)-N-(2-Dodecyl) propargylamine.

26. A pharmaceutical composition according to claim 19 wherein the propargylamine is a chiral compound and is the R-enantiomer.

27. A pharmaceutical composition for treating cancer comprising a combination of effective amounts of an antineoplastic drug and Rasagiline.

28. A method according to claim 2, wherein y is 1.

29. A method according to claim 4, wherein y is 1.

30. A method according to claim 2, wherein the propargylamine is selected from the group consisting of N-(1-Propyl) N-methylpropargylamine; N-(2-Propyl) N methylpropargylamine, N-(1-Butyl) N-methylpropargylamine; N-(1-Pentyl) N methylpropargylamine; N-(1-Hexyl) N-methylpropargylamine; N-(1-Heptyl) N methylpropargylamine; N-(1-Octyl) N-methylpropargylamine; N-(1-Nonyl) N methylpropargylamine; N-(1-Decyl) N-methylpropargylamine; N-(1-Undecyl) N methylpropargylamine; N-(1-Dodecyl) N-methylpropargylamine; (R)-N-(2-Butyl) N methylpropargylamine; (R)-N-(2-Pentyl) N-methylpropargylamine; (R)-N-(2-Hexyl) N methylpropargylamine; (R)-N-(2-Heptyl) N-methylpropargylamine; (R)-N-(2-Octyl) N methylpropargylamine; (R)-N-(2-Octyl) N-methylpropargylamine, (R)-N-(2-Decyl) N methylpropargylamine; (R)-N-(2-Undecyl) N-methylpropargylamine; and (R)-N-(2-Dodecyl) N-methylpropargylamine.

31. A method according to claim 2, wherein the propargylamine is selected from R-2-heptyl-methyl propargylamine (R-2HMP) and R-2-heptyl-propargylamine (R-2-HPA).

32. A method according to claim 4, wherein the propargylamine is selected from the group consisting of N-(1-Propyl) N-methylpropargylamine; N-(2-Propyl) N methylpropargylamine, N-(1-Butyl) N-methylpropargylamine; N-(1-Pentyl) N methylpropargylamine; N-(1-Hexyl) N-methylpropargylamine; N-(1-Heptyl) N methylpropargylamine; N-(1-Octyl) N-methylpropargylamine; N-(1-Nonyl) N methylpropargylamine; N-(1-Decyl) N-methylpropargylamine; N-(1-Undecyl) N methylpropargylamine; N-(1-Dodecyl) N-methylpropargylamine; (R)-N-(2-Butyl) N methylpropargylamine; (R)-N-(2-Pentyl) N-methylpropargylamine; (R)-N-(2-Hexyl) N methylpropargylamine; (R)-N-(2-Heptyl) N-methylpropargylamine; (R)-N-(2-Octyl) N methylpropargylamine; (R)-N-(2-Octyl) N-methylpropargylamine; (R)-N-(2-Decyl) N methylpropargylamine; (R)-N-(2-Undecyl) N-methylpropargylamine; and (R)-N-(2-Dodecyl) N-methylpropargylamine.

33. A method according to claim 4, wherein the propargylamine is selected from R-2-heptylmethyl propargylamine (R-2HMP) and R-2-heptyl-propargylamine (R-2-HPA).

34. A method according to claim 2, wherein the propargylamine is a chiral compound and is the R-enantiomer.

35. A method according to claim 4, wherein the propargylamine is a chiral compound and is the R-enantiomer.

36. A method according to claim 2, wherein the animal is human.

37. A method according to claim 4, wherein the animal is human.

38. A method according to claim 1, wherein the antineoplastic drug is selected from the group consisting of antimetabolites, alkylating agents, antimicrobial antineoplastics, antimicrotubule agents, cisplatinum and its derivatives and topoisomerase interactive agents.

39. A method according to claim 2, wherein the antineoplastic drug is selected from the group consisting of antimetabolites, alkylating agents, antimicrobial antineoplastics, antimicrotubule agents, cisplatinum and its derivatives and topoisomerase interactive agents.

40. A method according to claim 4, wherein the antineoplastic drug is selected from the group consisting of antimetabolites, alkylating agents, antimicrobial antineoplastics, antimicrotubule agents, cisplatinum and its derivatives and topoisomerase interactive agents.

41. A method according to claim 1, wherein the antineoplastic drug is selected from the group consisting of adriamycin, bis (2-chloroethyl)-3-cyclohexyl-1-nitrosurea (BCNU) and 1-(2-chloroethyl)-3-cyclohexyl-1-nitrosourea (CCNU), bleomycin sulfate, camptothecin, carmustine, chlorambucil, cisplatinum, cyclophospamide, cytosine arabinoside, daunomycin/daunorubicin, dacarbazine, doxorubicin, 5-fluorouracil, melphalan, mitomycin, mitoxantrone hydrochloride, etoposide, streptozocin and taxol and taxol derivatives.

42. A method according to claim 2, wherein the antineoplastic drug is selected from the group consisting of adriamycin, bis (2-chloroethyl)-3-cyclohexyl-1-nitrosurea (BCNU) and 1-(2-chloroethyl)-3-cyclohexyl-1-nitrosourea (CCNU), bleomycin sulfate, camptothecin, carmustine, chlorambucil, cisplatinum, cyclophospamide, cytosine arabinoside, daunomycin/daunorubicin, dacarbazine, doxorubicin, 5-fluorouracil, melphalan, mitomycin, mitoxantrone hydrochloride, etoposide, streptozocin and taxol and taxol derivatives.

43. A method according to claim 1, wherein the antineoplastic drug is selected from the group consisting of adriamycin, bis (2-chloroethyl)-3-cyclohexyl-1-nitrosurea (BCNU) and 1-(2-chloroethyl)-3-cyclohexyl-1-nitrosourea (CCNU), bleomycin sulfate, camptothecin, carmustine, chlorambucil, cisplatinum, cyclophospamide, cytosine arabinoside, daunomycin/daunorubicin, dacarbazine, doxorubicin, 5-fluorouracil, melphalan, mitomycin, mitoxantrone hydrochloride, etoposide, streptozocin and taxol and taxol derivatives.

44. A method according to claim 1, wherein the antineoplastic drug is selected from the group consisting of cytosine arabinoside, cis-platinum, cyclophospamide, adriamycin, daunomycin, vinblastine and 5-fluorouracil.

45. A method according to claim 2, wherein the antineoplastic drug is selected from the group consisting of cytosine arabinoside, cis-platinum, cyclophospamide, adriamycin, daunomycin, vinblastine and 5-fluorouracil.

46. A method according to claim 4, wherein the antineoplastic drug is selected from the group consisting of cytosine arabinoside, cis-platinum, cyclophospamide, adriamycin, daunomycin, vinblastine and 5-fluorouracil.

47. A method according to claim 6, wherein the antineoplastic drug is cis-platinum.

48. A method according to claim 9, wherein the antineoplastic drug is cis-platinum.

49. A method according to claim 31, wherein the antineoplastic drug is cis-platinum.

50. A method according to claim 33, wherein the antineoplastic drug is cis-platinum.

51. A method according to claim 16, wherein the cancer involves cells mutant in p53.

52. A method according to claim 51, wherein the cancer is selected from the group consisting of leukemias, lymphomas (Hodgkins and non-Hodgkins), lung and colorectal carcinomas, melanomas, ovarian cancer, testicular cancer and breast cancer.

53. A method according to claim 4, with the further proviso that the propargylamine is not rasagiline.

* * * * *